(12) United States Patent
Ferrante

(10) Patent No.: US 7,901,675 B2
(45) Date of Patent: Mar. 8, 2011

(54) METHOD OF USING COENZYME $Q_{10}$ TO TREAT HUNTINGTON'S DISEASE

(75) Inventor: Robert J. Ferrante, Canton, MA (US)

(73) Assignee: U.S. Department of Veterans Affairs, Washington, DC (US)

( * ) Notice: Subject to any disclaimer, the term of this patent is extended or adjusted under 35 U.S.C. 154(b) by 669 days.

(21) Appl. No.: 11/246,270

(22) Filed: Oct. 11, 2005

(65) Prior Publication Data

US 2006/0078549 A1 Apr. 13, 2006

Related U.S. Application Data

(60) Provisional application No. 60/617,643, filed on Oct. 13, 2004.

(51) Int. Cl.
*A61K 38/43* (2006.01)
(52) U.S. Cl. .................................... 424/94.1; 549/409
(58) Field of Classification Search .............. 549/409; 424/94.1
See application file for complete search history.

(56) References Cited

U.S. PATENT DOCUMENTS

| | | | |
|---|---|---|---|
| 4,684,520 A * | 8/1987 | Bertelli | 424/94.1 |
| 4,892,883 A | 1/1990 | Chatterjee et al. | |
| 6,045,826 A * | 4/2000 | Borowy-Borowski et al. | 424/451 |
| 6,399,089 B1 | 6/2002 | Yegorova et al. | |
| 2003/0012774 A1* | 1/2003 | Moldenhauer et al. | 424/94.3 |
| 2004/0077591 A1 | 4/2004 | Dangond | |
| 2004/0142859 A1 | 7/2004 | Steffan et al. | |
| 2009/0012175 A1 | 1/2009 | Bacopoulos et al. | |

FOREIGN PATENT DOCUMENTS

| WO | WO 03/032921 A2 | 4/2003 |
|---|---|---|
| WO | WO 03/047511 A3 | 6/2003 |

OTHER PUBLICATIONS

Shults, CW et al. Pilot trial of high dosages of coenzyme Q10 in patients with Parkinson's disease. Experimental Neurology. Available online Jun. 11, 2004. 188: 491-494.*
Smith, K., Matson, S., Cormier, K., Ryu, H., Hersch, S.M., Ferrante, R.J., Therapeutic effects of high dosage administration of coenzyme Q10 in the R6/2 model of Huntington's Disease. Presented on Oct. 24, 2004, at Society for Neuroscience Meeting, Oct. 23-27, 2004, San Diego, CA.
U.S. Appl. No. 11/058,297, filed Feb. 16, 2005, entitled Method of Ameliorating or Abrogating the Effects of a Neurodegenerative Disorder, such as Huntington's Disease, by Sodium Butyrate Chemotherapy.
Ferrante, RJ et al. Histone Deacetylase Inhibition by Sodium Butyrate Chemotherapy Ameliorates the Neurodegenerative Phenotype in Huntington's Disease Mice. The Journal of Neuroscience, Oct. 15, 2003, 23(28):9418-9427.
Ferrante RJ, Dedeoglu A, Kubilus J, Sugars KL, Rubinsztein DC, Ryu H, Beal MF, Ratan RR (2002b) Therapeutic effects of mithramycin in R6/2 transgenic Huntington's disease mice. SFN Abstr.
Ludolph, AC, Seelig M, Ludolph A, Novitt, P, Allen CN, Spencer PS, Sabri, MJ. 3-Nitropropionic Acid Decreases Cellular Energy Levels and Causes Neuronal Degeneration in Cortical Explants. Neurodegeneration 1:155-161 (1992).
Van Lint C, Emiliani S, Verdin E (1996) The Expression of a Small Fraction of Cellular Genes is Changed in Response to Histone Hyperacetylation. Gene Expr 5:245-253 (1996).
Hathcock, JN, Shao A. Risk assessment for coenzyme Q10 (Ubiquinone). Regulatory Toxicology and Pharmacology 45 (2006) 282-288.
Ikematsu H, Nakamura K, Harashima S, Fujii K, Fukutomi N. Safety assessment of coenzyme Q10 (Kaneka Q10) in healthy subjects: A double-blind, randomized, placebo-controlled trial. Regulatory Toxicology and Pharmacology 44 (2006) 212-218.
Ferrante, RJ, Ryu H, Kubilus JK, D'Mello S, Sugars KL, Lee J, Lu P, Smith K, Browne S, Beal MF, Kristal BS, Stavrovskaya IG, Hewett S, Rubinsztein DC, Langley B, Rata RR. Chemotherapy for the Brain: The Antitumor Antibiotic Mithramycin Prolongs Survival in a Mouse Model of Huntington's Disease. The Journal of Neuroscience, Nov. 17, 2004. 24(46):10335-10342.
Office Action dated Oct. 16, 2008, in U.S. Appl. No. 11/058,297, filed Feb. 16, 2005.
Feigin A et al. Assesment of Coenzyme $Q_{10}$ Tolerability in Huntington's Disease. Movement Disorders. vol. 11, No. 3, 1996, pp. 321-323.
Shults, CW et al. Absorption, tolerability, and effects on mitochondrial activity of oral coenzyme $Q_{10}$ in parkinsonian patients. Neurology—vol. 50, Issue 3 (Mar. 1998), pp. 793-795 (3 pages).
Alston, TA, Mela L, Bright MJ (1977) 3-Nitropropionate, the toxic substance of Indigofera, is a suicide inactivator of succinate dehydrogenase. Proc Natl Acad Sci 74: 3767-3771.
Andreassen OA, Ferrante RJ, Huang HM, Dedeoglu A, Park L, Ferrante KL, Kwon J, Borchelt DR, Ross CA, Gibson GE, Beal MF (2001) Dichloroacetate exerts therapeutic effects in transgenic mouse models of Huntington's disease. Ann Neurol 50: 112-117.
Andreassen OA, Ferrante RJ, Dedeoglu A, Beal MF(2001) Lipoic acid improves survival in transgenic mouse models of Huntington's disease. Neuroreport 12:3371-3374.
Beal MF (2000) Energetics in the pathogenesis of neurodegenerative diseases. Trends Neurosci 7:298-304.

(Continued)

*Primary Examiner* — Allison M. Ford
*Assistant Examiner* — Susan E. Fernandez
(74) *Attorney, Agent, or Firm* — Dinesh Agarwal, P.C.

(57) ABSTRACT

A method of ameliorating or abrogating the effects of a neurodegenerative disorder, such as Huntington's disease, includes administering a formulation including mitochondrial coenzyme $Q_{10}$ in a subject in need thereof. The formulation includes Hydro-Q Sorb®, which is a complex of coenzyme Q10 and cyclodextrin.

2 Claims, No Drawings

OTHER PUBLICATIONS

Beal MF, Brouillet E, Jenkins BG, Ferrante RJ, Kowall NW, Miller JM, Storey E, Srivastava R, Rosen BR, Hyman BT (1993) Neurochemical and histologic characterization of striatal excitotoxic lesions produced by the mitochondrial toxin 3-nitropropionic acid. J Neurosci 13: 4181-4192.

Bhalla, US, Ram PT, Iyengar R (2002) MAP kinase phosphatase as a locus of flexibility in a mitogen-activated protein kinase signaling network. Science 297:1018-1023.

Bhalla US, Iyengar R (1999) Emergent properties of networks of biological signaling pathways. Science 283:381-387.

Bogdanov MB, Andreassen OA, Dedeoglu A, Ferrante RJ, Beal MF (2001) Increased oxidative damage to DNA in a transgenic mouse model of Huntington's disease. J Neurochem 79:1246-1249.

Browne SE, Ferrante RJ, Beal MF (1999) Oxidative stress in Huntington's disease. Brain Pathol 9:147-163.

Brouillet E, Hantraye P, Ferrante RJ, Dolan R, Kowall NW, Beal MF (1995) Chronic mitochondrial energy impairment produces selective striatal degeneration and abnormal choreiform movements in primates. Proc Natl Acad Sci USA, 92:7105-7109.

Black AR, Jensen D, Lin SY, Azizkhan JC (1999) Growth/cell cycle regulation of Sp1 phosphorylation. J Biol Chem 274:1207-1215.

Brondello JM, Pouyssegur J, McKenzie FR (1999) Reduced MAP kinase phosphatase-1 degradation after p42/p44MAPK-dependent phosphorylation. Science. 286:2514-2517.

Butler LM, Agus DB, Scher HI, Higgins B, Rose A, Cordon-Cardo C, Thaler HT, Rifkind RA, Marks PA, Richon VM (2000) Suberoylanilide hydroxamic acid, an inhibitor of histone deacetylase, suppresses the growth of prostate cancer cells in vitro and in vivo. Cancer Res 60:5165-5170.

Candido EP, Reeves R, Davie JR (1978) Sodium butyrate inhibits histone deacetylation in cultured cells. Cell. 14:105-113.

Cha JH (2000) Transcriptional dysregulation in Huntington's disease. Trends Neurosci 23:387-392.

Chatterjee S, Zaman K, Ryu H, Conforto A, Ratan RR (2001) Sequence-selective DNA binding drugs mithramycin A and chromomycin A3 are potent inhibitors of neuronal apoptosis induced by oxidative stress and DNA damage in cortical neurons. Ann Neurol 49:345-354.

Chen M, Ona VO, Li M, Ferrante RJ, Fink KB, Zhu S, Bian J, Guo L, Farrell LA, Hersch SM, Hobbs W, Vonsattel JP, Cha JH, Friedlander RM (2000) Minocycline inhibits caspase-1 and caspase-3 expression and delays mortality in a transgenic mouse model of Huntington disease. Nat Med 6: 797-801.

Collins AF, Pearson HA, Giardina P, McDonagh KT, Brusilow SW, Dover GJ (1995) Oral sodium phenylbutyrate therapy in homozygous beta thalassemia: a clinical trial. Blood 85:43-49.

Dedeoglu A, Kubilus JK, Jeitner TM, Matson SA, Bogdanov M, Kowall NW, Matson WR, Cooper AJ, Ratan RR, Beal MF, Hersch SM, Ferrante RJ (2002) Therapeutic effects of cystamine in a murine model of Huntington's disease. J Neurosci 22:8942-8950.

Dedeoglu A, Kubilus JK, Yang L, Ferrante KL, Hersch SM, Beal MF, Ferrante RJ (2003) Creatine Therapy Provides Neuroprotection After Onset of Clinical Symptoms in Huntington's Disease Transgenic Mice. J Neurochem 85: 1359-1367.

Dunah AW, Jeong H, Griffin A, Kim YM, Standaert DG, Hersch SM, Mouradian MM, Young AB, Tanese N, Krainc D (2002) Sp1 and TAFII130 Transcriptional Activity Disrupted in Early Huntington's Disease. Science 296:2238-2243.

Egorin MJ, Yuan ZM, Sentz DL, Plaisance K, Eiseman JL (1999) Plasma pharmacokinetics of butyrate after intravenous administration of sodium butyrate or oral administration of tributyrin or sodium butyrate to mice and rats. Cancer Chemother Pharmacol 43:445-453.

Ferrante RJ, Andreassen OA, Jenkins BG, Dedeoglu A, Kuemmerle S, Kubilus JK, Kaddurah-Daouk R, Hersch SM, Beal MF (2000) Neuroprotective effects of creatine in a transgenic mouse model of Huntington's disease. J Neurosci 20:4389-97.

Ferrante RJ, Andreassen OA, Dedeoglu A, Ferrante KL, Jenkins BG, Hersch SM, Beal MF (2002a) Therapeutic effects of coenzyme Q10 and remacemide in transgenic mouse models of Huntington's disease. J Neurosci 22:1592-1599.

Ferrante RJ, Kubilus JK, Lee J, Ryu H, Beesen A, Zucker B, Smith K, Kowall NW, Ratan RR, Luthi-Carter R, Hersch SM (2003) Histone Deacetylase Inhibition by Sodium Butyrate Chemotherapy Ameliorates the Neurodegenerative Phenotype in Huntington's Disease Mice. J Neurosci 23(28):9418-9427.

Friedlander RM (2003) Apoptosis and caspases in neurodegenerative diseases. N Engl J Med 348:1365-1375.

Hamilton B F, Gould DH (1987) Nature and distribution of brain lesions in rats intoxicated with 3-nitropropionic acid: a type of hypoxic (energy deficient) brain damage. Acta Neuropathol 72: 286-297.

Hockly E, Richon VM, Woodman B, Smith DL, Zhou X, Rosa E, Sathasivam K, Ghazi-Noori S, Mahal A, Lowden PA, Steffan JS, Marsh JL, Thompson LM, Lewis CM, Marks PA, Bates GP (2003) Suberoylanilide hydroxamic acid, a histone deacetylase inhibitor, ameliorates motor deficits in a mouse model of Huntington's disease. Proc Natl Acad Sci U S A 100:2041-2046.

Holbert S, Denghien I, Kiechle T, Rosenblatt A, Wellington C, Hayden MR, Margolis RL, Ross CA, Dausset J, Ferrante RJ, Neri C (2001) The Gln-Ala repeat transcriptional activator CA150 interacts with huntingtin: neuropathologic and genetic evidence for a role in Huntington's disease pathogenesis. Proc Natl Acad Sci U S A 98:1811-1816.

Holbert S, Dedeoglu A, Humbert S, Saudou F, Ferrante RJ, Neri C (2003) Cdc42-interacting protein 4 binds to huntingtin: neuropathologic and biological evidence for a role in Huntington's disease. Proc Natl Acad Sci U S A 100:2712-2717.

Karpuj MV, Becher MW, Springer JE, Chabas D, Youssef S, Pedotti R, Mitchell D, Steinman L (2002) Prolonged survival and decreased abnormal movements in transgenic model of Huntington disease, with administration of the transglutaminase inhibitor cystamine. Nat Med 8:143-149.

Krainc D, Bai G, Okamoto S, Cartes M, Kusiak JW, Brent RN, Lipton SA (1998) Synergistic activation of the N-methyl-D-aspartate receptor subunit 1 promoter by myocyte enhancer factor 2C and Sp1. J Biol Chem 273:26218-26224.

Kuemmerle S, Gutekunst CA, Klein AM, Li XJ, Li SH, Beal MF, Hersch SM, Ferrante RJ (1999) Huntington aggregates may not predict neuronal death in Huntington's disease. Ann Neurol 46: 842-849.

Li J, Gorospe M, Hutter D, Barnes J, Keyse SM, Liu Y (2001) Transcriptional induction of MKP-1 in response to stress is associated with histone H3 phosphorylation-acetylation. Mol Cell Biol. 23:8213-8224.

Li SH, Cheng AL, Zhou H, Lam S, Rao M, Li H, Li XJ (2002) Interaction of Huntington disease protein with transcriptional activator Sp1. Mol Cell Biol 22:1277-1287.

Livak KJ and Schmittgen TD (2001) Analysis of relative gene expression data using real-time quantitative PCR and the 2(-Delta Delta C(T)) Methods 25:402-408.

Ludolph AC, He F, Spencer PS (1991) 3-Nitropropionic acid-exogenous animal neurotoxin and possible human striatal toxin. Can J Neurol Sci 18:492-498.

Luthi-Carter R, Strand A, Peters NL, Solano SM, Hollingsworth ZR, Menon AS, Frey AS, Spektor BS, Penney EB, Schilling G, Ross CA, Borchelt DR, Tapscott SJ, Young AB, Cha JH, Olson JM (2000) Decreased expression of striatal signaling genes in a mouse model of Huntington's disease. Hum Mol Genet 9:1259-1271.

Luthi-Carter R, Hanson SA, Strand AD, Bergstrom DA, Chun W, Peters NL, Woods AM, Chan EY, Kooperberg C, Krainc D, Young AB, Tapscott SJ, Olson JM (2002) Dysregulation of gene expression in the R6/2 model of polyglutamine disease: parallel changes in muscle and brain. Hum Mol Genet 11:1911-1926.

Mammen PP, Shelton JM, Goetsch SC, Williams SC, Richardson JA, Garry MG, Garry DJ (2002) Neuroglobin, a novel member of the globin family, is expressed in focal regions of the brain. J Histochem Cytochem 50:1591-1598.

McCampbell A, Taylor JP, Taye AA, Robitschek J, Li M, Walcott J, Merry D, Chai Y, Paulson H, Sobue G, Fischbeck KH (2000) CREB-binding protein sequestration by expanded polyglutamine. Hum Mol Genet 9: p. 2197-2202.

McCampbell A, Taye AA, Whitty L, Penney E, Steffan JS, Fischbeck KH (2001) Histone deacetylase inhibitors reduce polyglutamine toxicity. Proc Natl Acad Sci U S A 98:15179-15184.

Miller AA, Kurschel E, Osieka R, Schmidt CG (1987a) Clinical pharmacology of sodium butyrate in patients with acute leukemia. Eur J Cancer Clin Oncol 23:1283-1287.

Miller DM, Polansky DA, Thomas SD, Ray R, Campbell VW, Sanchez J, Koller CA (1987b) Mithramycin selectively inhibits transcription of G-C containing DNA. Am J Med Sci 294:388-394.

Nakamura K, Jeong SY, Uchihara T, Anno M, Nagashima K, Nagashima T, Ikeda S, Tsuji S, Kanazawa I (2001) SCA17, a novel autosomal dominant cerebellar ataxia caused by an expanded polyglutamine in TATA-binding protein. Hum Mol Genet 10:1441-1448.

Nemenoff RA, Winitz S, Qian NX, Van Putten V, Johnson GL, Heasley LE (1993) Phosphorylation and activation of a high molecular weight form of phospholipase A2 by p42 microtubule-associated protein 2 kinase and protein kinase C. J Biol Chem 268:1960-1964.

Nishibe S, Wahl MI, Hernandez-Sotomayor SM, Tonks NK, Rhee SG, Carpenter G (1990) Increase of the catalytic activity of phospholipase C-gamma 1 by tyrosine phosphorylation. Science 250:1253-1256.

Novelli A, Reilly JA, Lysko PG, Henneberry RC (1988) Glutamate becomes neurotoxic via the N-methyl-D-aspartate receptor when intracellular energy levels are reduced. Brain Res 451:205-212.

Nucifora FC, Jr, Sasaki M, Peters MF, Huang H, Cooper JK, Yamada M, Takahashi H, Tsuji S, Troncoso J, Dawson VL, Dawson TM, Ross CA (2001) Interference by huntingtin and atrophin-1 with cbp-mediated transcription leading to cellular toxicity. Science 291: 2423-2428.

Ohyagi Y, Yamada T, Goto I (1994) Hemoglobin as a novel protein developmentally regulated in neurons. Brain Res 635:323-327.

Perrine SP, Miller BA, Faller DV, Cohen RA, Vichinsky EP, Hurst D, Lubin BH, Papayannopoulou T (1989) Sodium butyrate enhances fetal globin gene expression in erythroid progenitors of patients with Hb SS and beta thalassemia. Blood 74:454-459.

Preisinger E, Jordan BM, Kazantsev A, Housman D (1999) Evidence for a recruitment and sequestration mechanism in Huntington's disease. Philos Trans R Soc Lond B Biol Sci 354: 1029-1034.

Richon VM, Sandhoff TW, Rifkind RA, Marks PA (2000) Histone deacetylase inhibitor selectively induces p21WAF1 expression and gene-associated histone acetylation. Proc Natl Acad Sci 97:10014-10019.

Ryu H, Lee J, Olofsson BA, Mwidau A, Deodoglu A, Escudero M, Flemington E, Azizkhan-Clifford J, Ferrante RJ, Ratan RR (2003a) Histone deacetylase inhibitors prevent oxidative neuronal death independent of expanded polyglutamine repeats via an Sp1-dependent pathway. Proc Natl Acad Sci USA 100:4281-4286.

Ryu H, Lee JH, Zaman K, Ferrante RJ, Ross BD, Neve R, Ratan RR (2003b) Sp1 and Sp3 are oxidative stress-inducible, anti-death transcription factors in cortical neurons. J. Neurosci 23:3597-3606.

Sealy L and Chalkley R (1978 )The effect of sodium butyrate on histone modification. Cell 14:115-121.

Sisodia SS (1998) Nuclear inclusions in glutamine repeat disorders: Are they pernicious, coincidental, or beneficial? Cell 95: 1-4.

Steffan JS, Kazantsev A, Spasic-Boskovic O, Greenwald M, Zhu YZ, Gohler H, Wanker EE, Bates GP, Housman DE, Thompson LM (2000) The Huntington's disease protein interacts with p53 and CREB-binding protein and represses transcription. Proc Natl Acad Sci USA 97:6763-6768.

Steffan JS, Bodai L, Pallos J, Poelman M, McCampbell A, Apostol BL, Kazantsev A, Schmidt E, Zhu YZ, Greenwald M, Kurokawa R, Housman DE, Jackson GR, Marsh JL, Thompson LM (2001) Histone deacetylase inhibitors arrest polyglutamine-dependent neurodegeneration in Drosophila. Nature 413: 739-743.

Struhl K (1998) Histone acetylation and transcriptional regulatory mechanisms. Genes Dev 12:599-606.

Sugars KL and Rubinsztein DC (2003) Transcriptional abnormalities in Huntington disease. TRENDS in Genetics 19: 233-238.

Sun Y, Jin K, Peel A, Mao XO, Xie L, Greenberg DA (2003) Neuroglobin protects the brain from experimental stroke in vivo. Proc Natl Acad Sci U S A 100: 3497-3500.

Tabrizi SJ, Workman J, Hart PE, et al. (2000) Mitochondrial dysfunction and free radical damage in the Huntington R6/2 transgenic mouse. Ann Neurol 47: 80-86.

Warrell RP, Jr., He, LZ, Richon V, Calleja E, Pandolfi PP (1998) Therapeutic targeting of transcription in acute promyelocytic leukemia by use of an inhibitor of histone deacetylase. J Natl Cancer Inst 90: 1621-1625.

Wood KW, Sarnecki C, Roberts TM, Blenis J (1992) Ras mediates nerve growth factor receptor modulation of three signal-transducing protein kinases: MAP kinase, Raf-1, and RSK.Cell 68:1041-1050.

Wu ZL, O'Kane TM, Scott RW, Savage MJ, Bozyczko-Coyne D (2002) Protein tyrosine phosphatases are up-regulated and participate in cell death induced by polyglutamine expansion. J Biol Chem 77:44208-44213.

Vigushin DM, Coombes RC (2002) Histone deacetylase inhibitors in cancer treatment. Anticancer Drugs 13:1-13.

Ryu, Hoon, et al., Sodium phenylbutyrate prolongs survival and regulates expression of anti-apoptotic genes in transgenic amyotrophic lateral sclerosis mice, Journal of Neurochemistry, 2005, 93, 1087-1098.

Rowland, L. & Shneider, N. Amyotrophic lateral sclerosis. *N. Engl. J. Med.* 344, 1688-1700 (2001).

Bensimon G, Lacomblez L, Meininger V & the ALS/Riluzole Study Group. A controlled trial of Riluzole in amyotrophic lateral sclerosis. *N. Eng. J. Med.* 330, 585-591(1994).

Miller, R.G, Mitchell, J.D., Lyon, M. & Moore, D.H. Riluzole for amyotrophic lateral sclerosis (ALS)/motor neuron disease (MND). *Amyotroph. Lateral Scler. Other Motor Neuron Disord.* 4, 191-206 (2003).

Rosen, D.R. et al. Mutations in Cu/Zn superoxide dismutase are associated with familial amyotrophic lateral sclerosis. *Nature* 362, 59-62 (1993).

Brown, R.H. Jr, & Robberecht, W. Amyotrophic lateral sclerosis: pathogenesis. *Semin. Neurol.* 21,131-139 (2001).

Andersen, P.M. et al. Sixteen novel mutations in the Cu/Zn superoxide dismutase gene in amyotrophic lateral sclerosis: a decade of discoveries, defects and disputes. *Amyotroph. Lateral Scler. Other Motor Neuron Disord.* 4, 62-73 (2003).

Gurney M. F. et al. Motor neuron degeneration in mice that express a human Cu,Zn superoxide dismutase mutation. *Science* 264, 1772-1775 (1994).

Ripps, M.E., Huntley, G.W., Hof, P.R., Morrison, J.H. & Gordon, J.W. Transgenic mice expressing an altered murine superoxide dismutase gene provide an animal model of amyotrophic lateral sclerosis. *Proc. Natl. Acad. Sci.* USA 92, 689-693 (1995).

Bruijn, L. et al. ALS-linked SOD1 mutant G85R mediates damage to astrocytes and promotes rapidly progressive disease with SOD1-containing inclusions. *Neuron* 18, 327-338 (1997).

Drachman, D.B. et al. Cyclooxygenase 2 inhibition protects motor neurons and prolongs survival in a transgenic mouse model of ALS. *Ann. Neurol.* 52, 771-778 (200).

Kieran, D. et al., Treatment with arimoclomol, a coinducer of heat shock proteins, delays disease progression in ALS mice. *Nat. Med.* 10, 402-405 (2004).

Klivenyi, P. et al. Neuroprotective effects of creatine in a transgenic animal model of amyotrophic lateral sclerosis. *Nat. Med.* 5, 347-350 (1999).

Zhu S. et al. Minocycline inhibits cytochrome c release and delays progression of amyotrophic lateral sclerosis in mice. *Nature* 417, 74-78 (2002).

Cleveland, D.W. & Rothstein, J.D. From Charcot to Lou Gehrig: Deciphering selective motor neuron death in ALS. *Nat. Neurosci. Rev.* 2, 806-819 (2001).

Pasinelli, P., Houseweart, M., Brown, R. & Cleveland, D. Caspase-1 and -3 are sequentially activated in motor neuron death in Cu/Zn superoxide dismutase mediated familial amyotrophic lateral sclerosis. *Proc. Natl. Acad. Sci.* USA 97, 13901-13906 (2000).

Kostic, V., Jackson-Lewis, V., de Bilbao, F., Dubois-Dauphin, M. & Przedborski, S. Bcl-2: Prolonging Life in a Transgenic Mouse Model of Familial Amyotrophic Lateral Sclerosis. *Science* 277, 559-562 (1997).

Vukosavic, S. et al. Delaying caspase activation by Bcl-2: A clue to disease retardation in a transgenic mouse model of amyotrophic lateral sclerosis. *J. Neurosci.* 20, 9119-9125 (2003).

Wakabayashi, K. et al. Bcl-2 related proteins are dramatically induced at the early stage of differentiation in human liver cancer cells by a histone deacetylase inhibitor projecting an anti-apoptotic role during this period. *Oncol. Rep.* 7, 285-288 (2000).

Malaspina, A., Kaushik, N. & de Belleroche, J. Differential expression of 14 genes in amyotrophic lateral sclerosis spinal cord detected using gridded cDNA arrays. *J. Neurochem.* 77, 132-145 (2001).

Ishigakia, S. et al. Differentially expressed genes in sporadic amyotrophic lateral sclerosis spinal cords screening by molecular indexing and subsequent cDNA microarray analysis. *FEBS Lett.* 531, 354-358 (2002).

Gonzalez de Aguilar, J.G. et al. Alteration of the Bcl-x/Bax ratio in a transgenic mouse model of amyotrophic lateral sclerosis: evidence for the implication of the p53 signaling pathway. *Neurobiol. Disease* 7, 406-415 (2000).

Yoshihara, T. et al. Differential expression of inflammation-and apoptosis-related genes in spinal cords of a mutant SOD1 transgenic mouse model of familial amyotrophic lateral sclerosis. *J. Neurochem.* 80, 158-167 (2002).

Olsen, M.K. et al. Disease mechanisms revealed by transcription profiling in SOD1-G93A transgenic mouse spinal cord. *Ann. Neurol.* 50, 730-740 (2001).

Dangond, F. et al. The molecular signature of late-stage human ALS revealed by expression profiling of post-mortem spinal cord gray matter. *Physiol. Genomics* 16, 229-239 (2004).

Cremer JE, Lai JC, Sarna GS. Rapid blood-brain transport and metabolism of butyrate and pyruvate in the rat after portocaval anastomosis. *J. Physio.* 266, 70P-71P (1977).

Mayo, M.W. et al. Ineffectiveness of histone deacetylase inhibitors to induce apoptosis involves the transcriptional activation of NF-B through the Akt pathway. *J. Biol. Chem.* 278, 18980-18989 (2003).

Mu, X., He, J., Anderson, D.W., Trojanowski, J.Q., & Springer, J.E.Altered expression of bcl-2 and bax mRNA in amyotrophic lateral sclerosis spinal cord motor neurons. *Ann. Neurol.* 40, 379-386 (1996).

ALS CNTF Study Group. A double-blind placebo-controlled clinical trial of subcutaneous recombinant human ciliary neurotrophic factor (rhCNTF) in amyotrophic lateral sclerosis. *Neurol.* 46, 1244-1249 (1996).

Cudkowicz, M. et al. A randomized, placebo-controlled trial of topiramate in amyotrophic lateral sclerosis. *Neurology* 61, 456-464 (2003).

Chang, J-G. et al. Treatment of spinal muscular atrophy by sodium butyrate. *Proc. Natl. Acad. Sci.* USA 98, 9808-9813 (2001).

Corcoran, L.J., Mitchison, T.J. & Liu, Q. A novel action of histone deacetylase inhibitors in a protein aggresome disease model. *Curr. Biol.* 14, 488-492 (2004).

Wang, C-Y., Mayo, M.W. & Baldwin, A.S. Jr. TNF- and cancer therapy-induced apoptosis: Potentiation by inhibition of NF-kappaB. *Science* 274, 784-787 (1996).

Kassed, C.A., Willing, A.E., Garbuzova-Davis, S., Sanberg, P.R. & Pennypacker, K.R. Lack of NF-kappaB p50 exacerbates degeneration of hippocampal neurons after chemical exposure and impairs learning. *Exp. Neurol.* 176, 277-288 (2002).

Pennypacker, K.R., Kassed, C.A., Eidizadeh, S., Saporta, S. & Sanberg, P.R. NF-B p50 is increased in neurons surviving hippocampal injury. *Exp. Neuro.* 172, 307-319 (2001).

Beg, A.A. & Baltimore, D. An essential role for NF-kappaB in preventing TNF-alpha-induced cell death. *Science* 274, 782-784 (1996).

Viatour, P. et al. NF- kappa B2/p100 induces Bcl-2 expression. *Leukemia* 17, 1349-1356 (2003).

Bowie, A. & O'Neil, L.A.J. Oxidative stress and nuclear factor-B activation. A reassessment of the evidence in the light of recent. *Biochem. Pharmacol.* 59, 13-23 (2000).

Chen, L., Fischle, W. Warner, V.E. & Greene, C. Duration of nuclear NF-kB action regulated by reversible acetylation. *Science* 293, 1653-1657 (2001).

Glaser, K.B. et al. Gene expression profiling of multiple histone deacetylase (HDAC) inhibitors: defining a common gene set produced by HDAC inhibition in T24 and MDA carcinoma cell lines. *Mol. Cancer Ther.* 2, 151-163 (2003).

Heckman, C.A., Mehew, J.W. & Boxer, L.M. NF-kappaB activates Bcl-2 expression in t(14;18) lymphoma cells. *Oncogene* 21, 3898-3908 (2001).

Gilbert, J. et al. A Phase I dose escalation and bioavailability study of oral sodium phenylbutyrate in patients with refractory solid tumor malignancies. *Clin. Cancer Res.* 7, 2292-2300 (2001).

Warrell, R.P. et al. Therapeutic targeting of transcription in acute promyelocytic leukemia by use of an inhibitor of histone deacetylase. *J. Natl. Cancer Inst.* 90, 1621-1625 (1998).

Ferrante, R.J., Klein, A.M., Dedeoglu, A. & Beal, M.F. Therapeutic efficacy of Ebb761 (Gingko Biloba Extract) in a transgenic mouse model of amyotrophic lateral sclerosis. *J. Mol. Neurosci.* 17, 89-96 (2001).

Barneoud, P. & Curet, O. Beneficial effects of lysine acetylsalicylate, a soluble salt of aspirin, on motor performance in a transgenic model of amyotrophic lateral sclerosis. *Exp. Neurol.* 155, 243-251 (1999).

U.S. Appl. No. 11/304,612, filed Dec. 16, 2005.

PCT International Search Report in International App. No. PCT/US02/37988 (1 pg.), May 23, 2003.

PCT International Preliminary Examination Report in International App. No. PCT/US02/37988 (4 pg), Sep. 8, 2003.

Bruno et al. Regeneration of Motor Nerves in Bilobalide-treated rats. Planta Med, Aug. 1993, pp. 302-307.

Silani et al. Nutritional Management in Amyotrophic Lateral Sclerosis: A Worldwide Perspective, J. Neurol., Aug. 1998.

Moldawer and Sattler. Human Immunodeficiency Virus-associated Wasting and Mechanisms of Cachexia Associated with Inflammation. Semin Oncol. Feb. 1998, pp. 73-81.

Defeudis and Drieu. Ginko Biloba Extract (EGb 761) and CNS Functions: Basic Studies and Clinical Applications, Current Drug Targets, Jul. 2000, pp. 44-49.

Office Action dated Jun. 26, 2007, in U.S. Appl. 10/495,335, filed May 12, 2004.

Office Action dated Jan. 13, 2010, in U.S. Appl. No. 11/304,612, filed Dec. 16, 2005.

\* cited by examiner

METHOD OF USING COENZYME $Q_{10}$ TO TREAT HUNTINGTON'S DISEASE

CROSS-REFERENCE TO RELATED APPLICATIONS

The present application claims priority on prior U.S. Provisional Application Ser. No. 60/617,643, filed Oct. 13, 2004, which is hereby incorporated herein in its entirety by reference.

STATEMENT REGARDING FEDERALLY SPONSORED RESEARCH OR DEVELOPMENT

The work leading to the present invention was supported by one or more grants from the U.S. Government. The U.S. Government therefore has certain rights in the invention.

FIELD AND BACKGROUND OF THE INVENTION

The present invention is generally directed to the treatment of neurodegenerative disorders, and more particularly to a method of ameliorating or abrogating the effects of Huntington's disease (HD) by using coenzyme $Q_{10}$.

Huntington's disease (HD) is a progressive and fatal neurological disorder that is caused by an expanded CAG repeat in a gene coding for a protein of unknown function, huntingtin. There are no current drug therapies proven to help ameliorate or abrogate the disease process in HD. Although the exact cause of the selective neuronal death in HD remains unknown, it has been postulated that aberrant protein-protein interactions, including aggregation of the mutant huntingtin protein, may be toxic to neurons and lead to oxidative stress, mitochondrial dysfunction, apoptosis, energy metabolism defects, and excitotoxicity.

Coenzyme $Q_{10}$ ($CoQ_{10}$) or ubiquinone is essentially a vitamin or vitamin-like substance. It is found naturally in foods, and is also sometimes synthesized in the body. Coenzymes are cofactors upon which the comparatively large and complex enzymes depend for their function. Coenzyme $Q_{10}$ is the coenzyme for at least three mitochondrial enzymes (complexes I, II, and III) as well as enzymes in other parts of the cell. Mitochondrial enzymes are essential for the production of the high-energy phosphate, adenosine triphosphate (ATP) upon which all cellular functions depend.

There is substantial evidence that bioenergetic defects may play a role in the pathogenesis of HD. A possible therapy for diseases in which there is defective energy metabolism is to administer the mitochondrial cofactor coenzyme $Q_{10}$ ($CoQ_{10}$). We have previously demonstrated that oral administration of $CoQ_{10}$ (400 mg/kg) was neuroprotective in R6/2 mice (14.5% survival extension).

In my co-pending application Ser. Nos. 60/545,532, filed Feb. 19, 2004, and 11/058,297, filed Feb. 16, 2005, both entitled METHOD OF AMELIORATING OR ABROGATING THE EFFECTS OF A NEURODEGENERATIVE DISORDER, SUCH AS HUNTINGTON'S DISEASE, BY SODIUM BUTYRATE CHEMOTHERAPY (both hereby incorporated herein in their entirety by reference) the effects of intraperitoneal administration of histone deacetylase (HDAC) inhibitor, such as sodium butyrate, on HD pathogenesis was shown. The present invention is directed to the effects of coenzyme $Q_{10}$ on HD pathogenesis.

OBJECTS AND SUMMARY OF THE INVENTION

The principal object of the present invention is to provide a method of ameliorating or abrogating the effects a neurodegenerative disorder, such as Huntington's disease, by using coenzyme $Q_{10}$.

An object of the present invention is to provide a method of ameliorating or abrogating the effects of a neurodegenerative disorder, such as Huntington's disease, by high dose administration of coenzyme $Q_{10}$.

Another object of the present invention is to increase survival, neuroprotection, improve motor performance, and/or prevent body weight loss by administering coenzyme $Q_{10}$ in a subject.

Yet another object of the present invention is to provide therapy for diseases in which there is defective energy metabolism by administering a mitochondrial cofactor coenzyme $Q_{10}$ in a subject.

An additional object of the present invention is to demonstrate therapeutic effects of high dose administration of coenzyme $Q_{10}$ in the R6/2 mice with Huntington's disease.

One of the above objects is met, in part, by the present invention which in one aspect includes ameliorating or abrogating the effects of a neurodegenerative disorder in a subject by administering a formulation comprising a mitochondrial coenzyme in a subject in need thereof.

Another aspect of the present invention includes preventing neuronal death in a subject having Huntington's disease by administering a formulation comprising a mitochondrial coenzyme in a subject in need thereof.

Another aspect of the present invention includes treating a subject having Huntington's disease by administering a formulation comprising mitochondrial coenzyme in a subject in need thereof.

Another aspect of the present invention includes protecting neural cells in a subject having a neurological disorder by increasing plasma level of $CoQ_{10}$ by administering a high dose of $CoQ_{10}$ in a subject in need thereof.

Another aspect of the present invention includes improving motor performance and/or reducing weight loss in a subject by administering a formulation comprising a mitochondrial coenzyme in a subject in need thereof.

Another aspect of the present invention includes increasing the level of $CoQ_{10}$ in the brain of a Huntington's disease mammal, such as a mouse, by administering a formulation including a complex of coenzyme $Q_{10}$ and gamma cyclodextrin.

Another aspect of the present invention includes increasing the level of adenosine triphosphate (ATP) in the brain of a Huntington's disease mammal, such as a mouse, by administering a formulation including a complex of coenzyme $Q_{10}$ and gamma cyclodextrin.

DETAILED DESCRIPTION OF THE PREFERRED EMBODIMENT(S) OF THE INVENTION

The present invention is based, in part, on the discovery that increased level of $CoQ_{10}$ appears to slow the progressive functional decline in Parkinson's disease. We orally administered $CoQ_{10}$ at 400 mg/kg, and 1, 5, 10, and 20 g/kg in R6/2 mice starting at weaning in chow formulations. $CoQ_{10}$ significantly extended survival at all doses in comparison to untreated R6/2 mice, with greatest survival extension at 5 g/kg (21.3%). $CoQ_{10}$ significantly delayed the development of weight loss, motor deficits, grip strength, brain atrophy, and huntingtin inclusions in R6/2 mice. As measured by HPLC, brain levels of $CoQ_{10}$ were significantly reduced in R6/2 mice, in comparison to wild type (WT) littermate control mice. A three week administration of a highly bioavailable formulation of $CoQ_{10}$, Hydro-Q Sorb® (1 g/kg, obtained from Tishcon Corp.) increased $CoQ_{10}$ plasma levels over three-hundred fold and significantly augmented brain levels by 16.2% in R6/2 mice to those levels observed in WT mice (Hydro-Q Sorb® is a complex of coenzyme $Q_{10}$ and gamma cyclodextrin). These preliminary findings show that higher dosing of $CoQ_{10}$ exerts a greater therapeutic benefit in a dose dependent manner in R6/2 HD mice and suggest that human clinical trials to determine whether increasing dose levels of $CoQ_{10}$ are safe, well tolerated, and slow the disease process in HD patients may be warranted.

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

What is claimed is:

1. A method of treating a subject having Huntington's disease, comprising:
   orally administering a formulation comprising a dose ranging from about 5 g/kg to 20 g/kg of coenzyme $Q_{10}$.
2. The method of claim 1, wherein:
   the formulation comprises a complex of coenzyme $Q_{10}$ and gamma cyclodextrin.

* * * * *